(12) United States Patent  
Remondi

(10) Patent No.: US 11,664,118 B2  
(45) Date of Patent: May 30, 2023

(54) DEVICE FOR BLOOD CONTAINER PROCESSING

(71) Applicant: Fresenius Kabi Deutschland GmbH, Bad Homburg (DE)

(72) Inventor: Fabio Remondi, Mirandola (IT)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 282 days.

(21) Appl. No.: 15/772,929

(22) PCT Filed: Feb. 27, 2017

(86) PCT No.: PCT/EP2017/054446  
§ 371 (c)(1),  
(2) Date: May 2, 2018

(87) PCT Pub. No.: WO2017/153191  
PCT Pub. Date: Sep. 14, 2017

(65) Prior Publication Data  
US 2018/0315501 A1 Nov. 1, 2018

(30) Foreign Application Priority Data  
Mar. 9, 2016 (EP) .................................... 16159339

(51) Int. Cl.  
*G16H 40/20* (2018.01)  
*A61M 1/02* (2006.01)  
(Continued)

(52) U.S. Cl.  
CPC ............. *G16H 40/20* (2018.01); *A61J 1/10* (2013.01); *A61M 1/0209* (2013.01);  
(Continued)

(58) Field of Classification Search  
CPC ............. G16H 10/40; G16H 10/087; G16H 40/20–40; G06Q 10/087; G06K 19/0721; A61J 1/16; A61J 1/165  
See application file for complete search history.

(56) References Cited

U.S. PATENT DOCUMENTS

| 9,764,075 B2 | 9/2017 | Blickhan et al. | |
| 2003/0018289 A1* | 1/2003 | Ng | G16H 10/20 210/782 |
| 2003/0040835 A1* | 2/2003 | Ng | A61B 5/150786 700/214 |
| 2004/0039749 A1* | 2/2004 | Yokozawa | G06K 19/07783 |

(Continued)

FOREIGN PATENT DOCUMENTS

| CN | 1808461 A | 7/2006 |
| CN | 101042723 A | 9/2007 |

(Continued)

OTHER PUBLICATIONS

Zarabzadeh et al., Implementation of an RFID-based Biological Sample Identification and Tracking System, 2011, IEEE International Conference on RFID-Technologies and Applications (Year: 2011).*

(Continued)

*Primary Examiner* — Shahid Merchant  
*Assistant Examiner* — Karen A Hranek  
(74) *Attorney, Agent, or Firm* — Cook Alex Ltd

(57) ABSTRACT

Device for blood container processing having a data storage reader unit 20 being adapted to read an blood donor identifier from a data storage of a blood container, and a data processing unit 50 being adapted to request for blood donor related information from an data base 163 based on the read blood donor identifier to allow a correct processing of all relevant information with respect to a blood (Continued)

donator and a blood recipient, to match the blood correctly and to avoid any serious injuries on the blood recipient side.

6 Claims, 3 Drawing Sheets

(51) Int. Cl.
| | | |
|---|---|---|
| *A61J 1/10* | (2006.01) | |
| *G06K 19/07* | (2006.01) | |
| *G06Q 10/087* | (2023.01) | |
| *G16Z 99/00* | (2019.01) | |
| *G16H 10/60* | (2018.01) | |

(52) U.S. Cl.
CPC ....... *G06K 19/0723* (2013.01); *G06Q 10/087* (2013.01); *G16H 10/60* (2018.01); *G16Z 99/00* (2019.02); *A61J 2205/60* (2013.01); *A61M 2205/60* (2013.01)

(56) References Cited

U.S. PATENT DOCUMENTS

| | | | | |
|---|---|---|---|---|
| 2004/0044326 | A1* | 3/2004 | Kranz | G16H 10/40 604/408 |
| 2004/0046020 | A1* | 3/2004 | Andreasson | A61J 1/14 235/385 |
| 2006/0178909 | A1* | 8/2006 | Hauck | G16H 40/20 705/28 |
| 2008/0088467 | A1* | 4/2008 | Al-Ali | A61B 5/6826 340/679 |
| 2008/0208750 | A1* | 8/2008 | Chen | G06Q 10/0833 340/572.1 |
| 2010/0049542 | A1* | 2/2010 | Benjamin | G06Q 10/0637 705/28 |
| 2016/0113721 | A1* | 4/2016 | Seremjian | G07F 17/0092 340/12.51 |
| 2017/0103363 | A1* | 4/2017 | Boukhny | G16H 40/63 |

FOREIGN PATENT DOCUMENTS

| | | | |
|---|---|---|---|
| CN | 101099712 B | * | 5/2012 |
| CN | 102567641 A | * | 7/2012 |
| CN | 102958545 A | | 3/2013 |
| CN | 103793867 A | | 5/2014 |
| WO | WO 96/36923 A1 | | 11/1996 |
| WO | WO 02/088930 A1 | | 11/2002 |

OTHER PUBLICATIONS

Jiang et al., A Dynamic Blood Information Management System Based on RFID, Sep. 2005, Engineering in Medicine and Biology 27th Annual Conference (Year: 2005).*
Adarsh, Effective Blood Bank Management Based on RFID in Real Time Systems, 2014, International Conference on Embedded Systems (Year: 2014).*
S. Gerald Sandler et al., Radiofrequency identification technology can standardize and document blood collections and transfusions, Transfusion, vol. 47, No. 5, pp. 763-770, May 1, 2007.
Zaric Andela et al., RFID-based Smart Blood Stock System, IEEE Antennas and Propagation Magazine, vol. 57, No. 2, pp. 54-65, Apr. 1, 2015.
International Search Report and Written Opinion, counterpart International Appl. No. PCT/EP2017/054446, dated May 4, 2017.
Office Action corresponding Chinese application No. 201780006184.4 (dated Mar. 25, 2021) (10 pages).

* cited by examiner

DEVICE FOR BLOOD CONTAINER PROCESSING

FIELD OF THE INVENTION

The present invention relates to a device for blood container processing, in particular to a MultiBag RFID device and software solution, in particular compatible with Fresenius Kabi's CompoMat G5/CompoMasterNet and CompoGuard/DonationMasterNet.

BACKGROUND OF THE INVENTION

RFID technology is becoming important in transfusion technology sector. It is an object to provide a device using RFID, replacing barcode and introducing new possibilities in automatic processing. Interest from market is growing because RFID technology in blood banks and transfusion medicine has the potential to improve operational efficiency and advance patient safety at point of care by automatically identifying, reconciling, and tracking blood products throughout the blood supply chain.

SUMMARY OF THE INVENTION

The invention provides a device for processing a blood container and a respective blood container according to the subject matter of the independent claims. Further embodiments are incorporated in the dependent claims.

According to an embodiment, there is provided a device for blood container processing, wherein the device comprises a receptacle for at least one blood container being equipped with a data storage tag, a data storage reader unit for reading a data storage of a data storage tag on a blood container, a data storage writing unit for writing a data storage of a data storage tag on a blood container, a user interface for inputting blood recipient related information, a data processing unit having a data storage reader interface, a data storage writer interface, an user input interface and a data base communicating interface, wherein the data storage reader unit is communicatively connected to the data storage reader interface, wherein the data storage writer unit is communicatively connected to the data storage writer interface, wherein the user interface is communicatively connected to the user input interface, wherein the data processing unit is communicatively connected to a data base having stored therein blood donor related information, wherein the data storage reading unit is adapted to read an blood donor identifier from a data storage of a blood container, wherein the data processing unit is adapted to request for blood donor related information from an data base based on the read blood donor identifier, wherein the data processing unit is adapted to request an data base for interrelated blood recipient and donor information based on the blood donor related information and the recipient related information input via the user interface, wherein the data processing unit is adapted to control the data storage writing unit to write blood donor related information into the data storage based on the interrelated blood recipient and donor information.

This allows a correct processing of all relevant information with respect to the blood donor and the blood recipient. The data base information may be used to match the blood correctly and to avoid any serious injuries on the blood recipient side. If the donor and the recipient are identified, the matching information can be stored on the container. When storing the donator and the recipient, any erroneous use can be avoided.

According to an embodiment, the interrelated blood recipient and donator information is information whether the donator blood matches the recipient.

Thus, the match of the donator and the recipient can directly be stored on the container.

According to an embodiment, the data storage unit is an RFID tag.

Thus, the information can be read contactless and without an energy supply on the container.

According to an embodiment, a data base for interrelated blood recipient and donator information is an external data base and a communicative connection between the device and a data base for interrelated blood recipient and donator information is a wireless connection.

Thus, even complex data volume or computational capacities of external entities may be used. Further, it is possible to use a data base which can be provided form outside with respective information, which can be used by different users, i.e. different devices for blood container processing at different locations.

According to an embodiment, a data base for blood donator related information is an external data base and a communicative connection between the device and a data base for blood donator related information is a wireless connection.

Thus the respective information can be provided even in very flexible situations and locations of the device for blood container processing.

According to an embodiment, the device further comprises a first data base storage unit having stored therein a data base for interrelated blood recipient and donator information.

Thus, the required information can also be provided locally without the need for an external access to a data base. In case the system does not have an external connection to a data base, the system can be protected against external access.

According to an embodiment, the device further comprises a second data base storage unit having stored therein a data base for blood donator related information.

Thus, the required information can also be provided locally without the need for an external access to a data base. In case the system does not have an external connection to a data base, the system can be protected against external access.

According to an embodiment, blood donator related information comprises at least one of the group, the group consisting of donator information, blood separation information, and blood component information.

Thus, relevant information for the compatibility of a donator and the recipient can be provided directly on the container.

According to an embodiment, the data storage reader unit has at least one data storage reading element and the data storage writer unit has at least one data storage writing element, wherein the data storage reading element and the data storage writing element are combined as a single reading writing unit so as to read and write a combined reading and writing data storage of a data storage tag on a blood container.

Thus, a compact reading and writing unit can be provided in order to handle reading and writing information from and to the blood container.

According to an embodiment, the receptacle is adapted for receiving a plurality of blood containers in parallel, wherein the data storage reader unit and the data storage writer unit are adapted to read and write the data storage tags of each of the plurality of blood containers in parallel.

Thus, a parallel processing can be conducted. The several reading and writing elements and/or units can be connected to a bus system so as to communicate with the data processing unit.

According to an embodiment, there is provided a blood container comprising a volume for receiving blood, a data storage tag, wherein the data storage tag comprises a reading data storage and a writing data storage.

Thus, the related information can directly be provided at the container, so that the information is immediately bound to the container.

According to an embodiment, the data storage tag is an RFID tag.

Thus, a contactless reading and writing can be achieved without the need for a power supply at the container.

According to an embodiment, the reading data storage and the writing data storage are realized as the same chip.

Thus, a compact design an thus a cost efficient chip can be provided.

According to an embodiment, the reading data storage and the writing data storage are realized different chips, wherein the reading chip is adapted to be blocked from being written by the writing mechanism which is used for writing the writing chip.

Thus, a higher data protection can be achieved. Different chips allow a better separation and thus different measures for reading and writing chips.

According to an embodiment, the reading data storage is capable of holding a blood donator identification.

Thus, a unique and optionally un-modifyable donator identification can be achieved.

According to an embodiment, the writing data storage is capable of holding an interrelated blood donator and recipient identification.

Thus, the relevant information can be provided on the container depending on the intended recipient. In case the recipient changes, the updated information can be written onto the writable data storage. As an alternative an "only write once" date storage can be provided, so that any modification can be avoided after writing the recipient relevant and interrelation relevant information onto the container.

DETAILED DESCRIPTION OF EXEMPLARY EMBODIMENTS OF THE INVENTION

Figure 1:
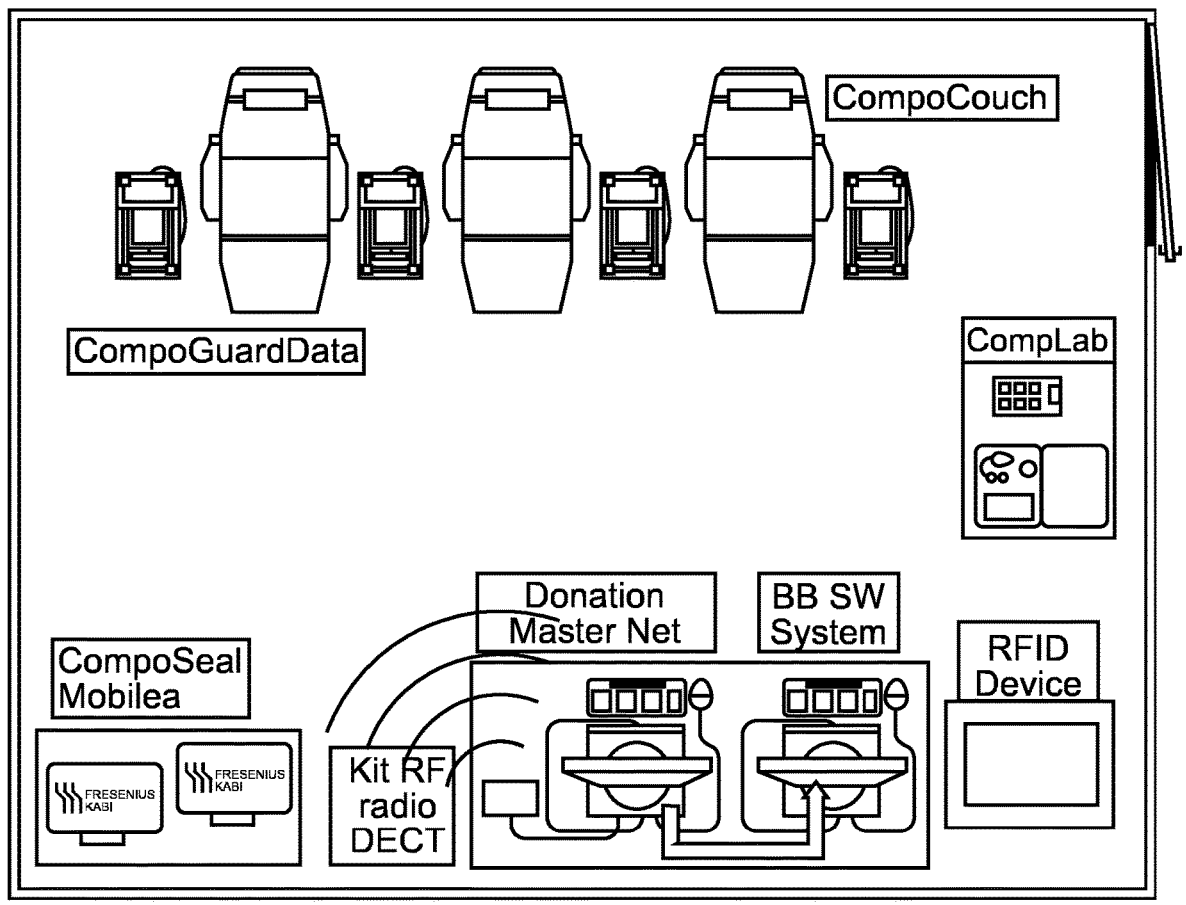
FIG. 1 illustrates a collection room with CompoGuard and DonationMasterNet SW.

In this specification the following abbreviations are used:
CG: CompoGuard (Mixing scale)
G5: CompoMat G5 (Whole Blood Separator)
DMNet: DonationMasterNet (CG Datamanagement)
CMNetG5: CompoMasterNet G5 (G5 Datamanagement)
BBSW: Blood Bank Software—Hospital or Blood Bank Datamanagement
MB RFID: MultiBag RFID Device
MB SW: MultiBag RFID Device Datamanagement
PLT: Platelets
BC: Buffy Coat
RCC: Red Cell Concentrate
DC: Donation Code
HC: Hemocomponent Code In this specification the following references are used:
1 device for blood container processing
10 receptacle
20 data storage reader unit
21 data storage reader interface
25 data storage reading element
30 data storage writing unit
31 data storage writer interface
35 data storage writing element
40 user interface
41 user input interface
50 data processing unit
60 data communication unit
61 data base communicating interface
62 first data base storage unit for interrelated blood recipient and donator inform.
63 second data base storage unit for blood donator related information
162 data base for interrelated blood recipient and donator information
163 data base for blood donator related information
200 blood container
210 volume of container for receiving blood
260 data storage tag on container
262 reading data storage
263 writing data storage The present invention provides a device for blood container processing. This device at least partially may be implemented as a MultiBag RFID reader-writer device (MB RFID) classified as MD according to 93/42/EEC. The device may further at least partially be implemented as a MultiBag RFID device data management solution (MB SW) being validated verified and documented according the regulatory from FDA according MD software, that will coordinate the read/write function of MB RFID device. The CG and G5 devices and their data management solution DMNet and CMNetG5 respectively, may for example not be modified in any case.

MB RFID may be implemented by a desktop device that is capable to read and write several bags in the same time with <<1% of error for RFID tags LRI 2K 55×55 (inlay 50×50); for further tags % error has to be evaluated but always below 1%. Maximum number of bags (1 bag=1 TAG) may be for example 25 bags. The linear dimensions of the MB RFID where bags can be placed may be for example a A3-format (30 cm×42 cm L×P). External dimensions of the MB RFID may be designed for example to not exceed 51 cm×65 cm×42 cm (L×P×H).

Figure 3:
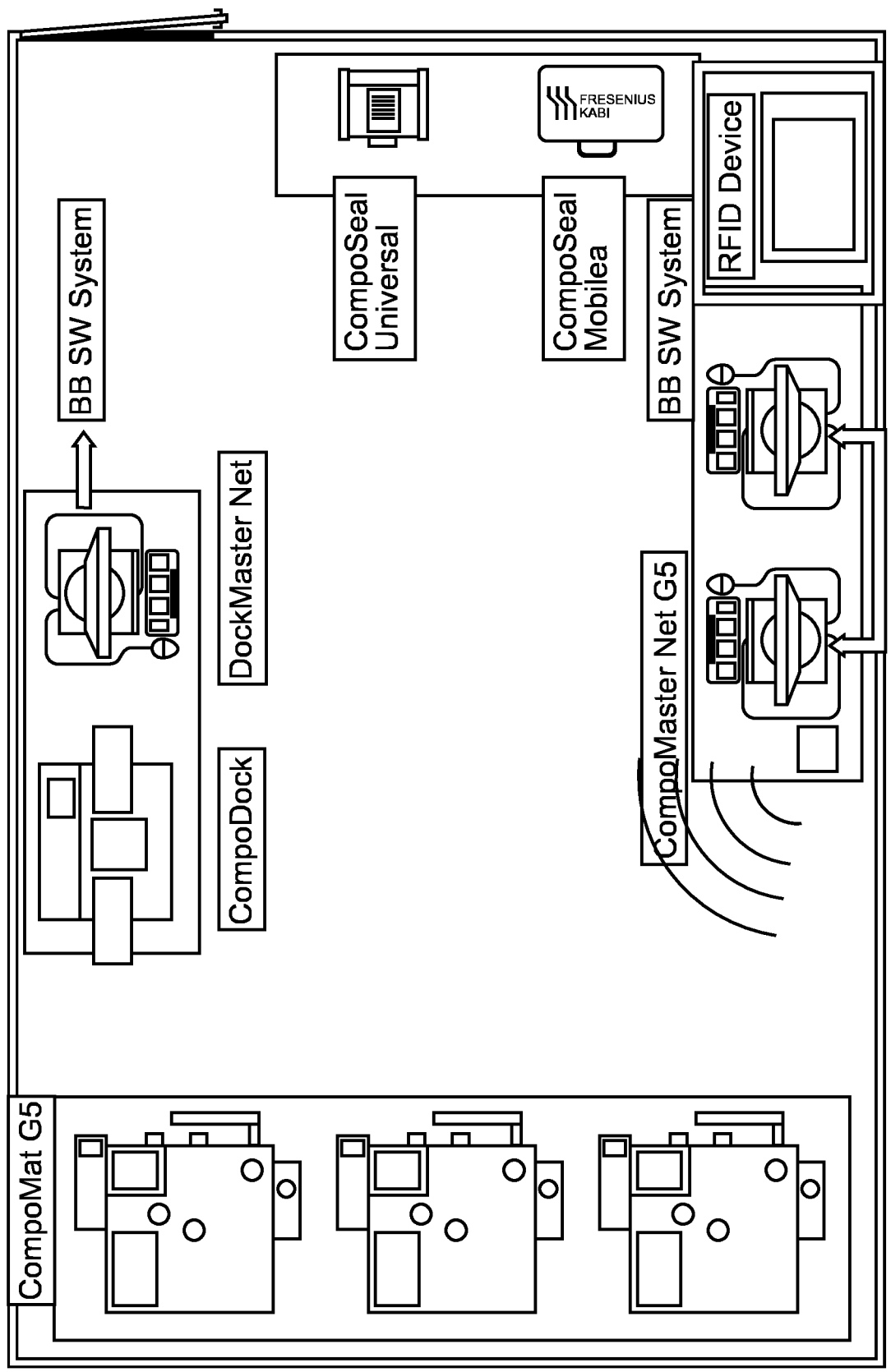
FIG. 3 illustrates a separation room with CompoMatG5 and CompoMasterNetG5 SW.

MB RFID may be linked to a personal computer or laptop whereas is installed its data manager software (MB SW). The DMNet and CMNet G5 may be for example installed not in the same PC or laptop, as illustrated in FIGS. 1 and 3.

MB SW may for example be able to communicate with DMNet, CMNet G5 and BB SW. This link may for example be done via serial port and/or USB 2.0/3.0 port and/or wireless protocol (WiFi). Communication between MB RFID and MB SW may be for example be bi-directional. After reading/writing function MB RFID may for example confirm the successful or unsuccessful action. Communication between MB RFID and BB SW may for example be bi-directional. Communication between MB SW and DMNet and CMNetG5 may for example be one-way mode: only pulling data from our DMNet and CMNetG5 to MB SW. MB SW has to pull the ASCII data from DMNet and CMNetG5. At the end of the procedures, DMNet and CMNetG5 may for example create automatically an ASCII file where a constant number of data fields per donation data record is exported. MB SW may for example store in itself these records, making a copy-paste of this file is directly take from DMnet or CMNet, or receiving this file from BB SW. This file for example cannot be deleted or modified from the original folder.

FIG. 1 illustrates a collection room with CompoGuard and DonationMasterNet SW. The collection room may include seats, referred to as CompoCouch, for blood donators. The donated blood may directly analyzed and monitored. The gained blood may be packed and sealed on site. The blood container may be provided with a unique identifier as well as with a storing tag, which will be described later with respect to FIG. 4. By providing the containers directly with identifiers on site, failures may be reduced in particular with respect to erroneous identification of the blood.

Figure 2:
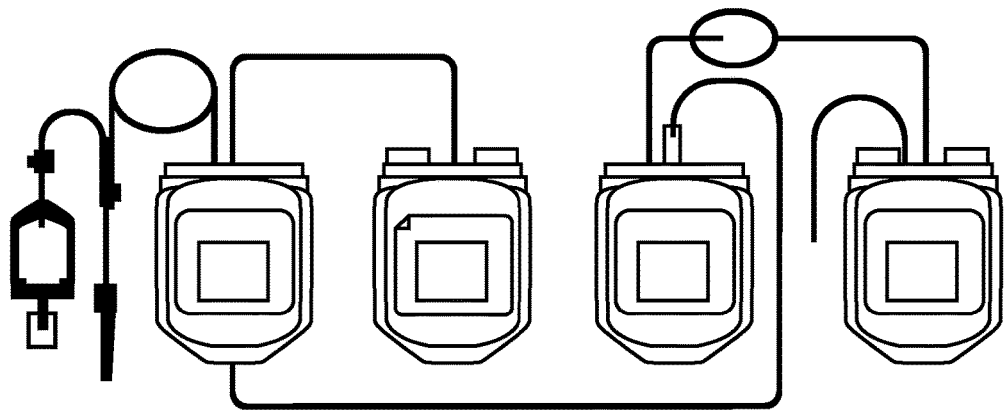
FIG. 2 illustrates an example of 4ple T&B with RCC InLine filter.

FIG. 2 illustrates an example of 4ple T&B with RCC InLine filter. The filter may provide a proper filtering process in order to filter the blood or blood plasma according to the respective requirements.

FIG. 3 illustrates a separation room with CompoMatG5 and CompoMasterNetG5 SW. The separation room may have all required facilities for a proper processing of the blood and the blood containers.

The workflow in the collection site may for example be as follows:
a. Label are printed in eye-readable barcode and written in RFID (with at least DC and HC) by one printer in connection with BB SW.
b. Bags are labelled (see FIG. 2 TAGs mainly on PLS and RCC bag. BC/PRP bag is an option).
c. Donation starts using Fresenius Kabi interface on CG.
d. DMNet receives the list of DC and other information that, in real time, send to all CG present in the network.
e. Simply reading DC, CG set itself on the right program with dedicated collection volume, barcode sequence, alarm settings.
f. At the end of the donation, CG send data into DMNet Software that create automatically an ASCII file where a constant number of 61 data fields per donation data record is exported. The fields are each separated by a semicolon ";". If no data are stored for one field, the field remains empty. The corresponding field length is zero.
g. MB SW stores in itself these records, making a copy-paste of this file that cannot be delete from the original folder because it's required also for the interface between DMNet and BB SW.
h. In MB SW is present a pre-setting phase where, based on the structure of the ASCII file received, is possible define which data has to be write on the TAG. For example interesting data could be only data present in position 6/7/11.
i. When a defined number of bags are positioning on the MB RFID using plastic trays, device reads DC codes written in the TAG and send this list into MB SW.
j. MB SW replies to the device with the corresponding list of data selected as described in phase h per each DC.

For example: Donation code 202500412536 has this ASCII output file:

1;1Donation;20100509122349;20100513081951; 20100521072416;201005220 81916;002CGA0277/ V1.4.0.1;0;255;480;481;0;335;40;0;100;0;106;568;0;0;0; 4;ABR,;BAG0,K202500412536;LOT,K7755234;OPE, M0034;TUB,K7755234;;;;;;;;;;;;;;;;;;;;;;;;;;;;;;;;;;;CRC, 0x0F9A, where the position in bold are those selected (position 6/7/11) in phase h.

So MB SW has to send to MB RFID a string as:
202500412536, 20100522081916;002CGA0277/V1.4.0.1, 481

This string as to be the same for each DC present on the MB RFID.

k. MB RFID writes in each TAG the correct string received from MB SW.
l. When bags have to be ship to blood bank, shipment list should be made by RFID massive reading, using MB RFID.

For example: Shipment box could be positioned over the MB RFID and the device communicates to MB SW how many and which bags are present.

The workflow in the separation site may for example be as follows:
FIG. 2 illustrates a separation room with CompoMatG5 and CompoMasterNetG5 SW:
a. Separation starts using Fresenius Kabi interface on G5.
b. CMNetG5 receives the list of DC that, in real time, send to all G5 present in the network.
c. Simply reading DC, G5 set itself on the right program depending on bag type, donation time, and, i.e. knows if it could produce BC for pool or for waste etc . . .
d. At the end of the separation, G5 send data into CMNetG5 that create automatically an .csv file where a constant number of 43 data fields per separation data record is exported. The fields are each separated by a semicolon ";". If no data are stored for one field, the field remains empty. The corresponding field length is zero.

For Example: printout .csv file:
"DonationBC","DummyBC","7CPT0017","09:19:18","09: 20:18","00:01:00","09/02/2009", "ResultBC " ,"12", "TestProgram12","Operator1BC","1","00:00:01", "001", "002","003","004","005","201","202","203","204", "205","1","ProductBC", "BatchBC","Operator2BC", "CentrifugeBC","AdditionalBC","Incidence1", "Incidence2", "Incidence3","Incidence4","Incidence5", "","","101","102","103","104", "105","09:19:18","09: 20:18"

e. MB SW may store in itself these records, making a copy-paste of this file that cannot be delete from the original folder because it's required also for the interface between CMNetG5 and BB SW.
f. In MB SW presents a pre-setting phase where, based on the structure of the .csv file received, should be possible define which Data for which hemocomponent has to be written in the TAG.

For example interesting data for plasma bag could be only data present in position 7/14 and for RCC bag could be only data in position 7/19.

g. When a defined number of bags are positioning on the MB RFID using plastic trays, device shall read DC and HC codes written in the TAG and send this list into MB SW.
h. MB SW shall reply to the device with the corresponding list of data selected as described in phase f. per each DC and HC.

For example: Code 202500412536 has this .csv output file: "K202500412536","","B","12:00:52","12:03:16","00:02: 24","30/07/2008","","3", "CQ32250","Operator1","0", "00:00:00","302","","","","","344","","","","","0", "KR8344","K08F06L51","","",""

Where the position in bold are those selected (position 7/14/19).

So MB SW has to send to MB RFID a string as:

202500412536, 30/07/2008;302;344

This string as to be the same for each DC present on the MB RFID i. MB RFID shall write in each TAG the correct string received from MB SW differentiating plasma and RCC bag.

For example:

Plasma bag with DC 202500412536 and HC 7 has to receive only 30/07/2008;302. RCC bag with DC 202500412536 and HC 25 has to receive only 30/07/2008;344 j. When bags have to be ship to hospital, shipment list should be made by RFID massive reading, using MB RFID.

For example shipment box could be positioned over the MB RFID and the device should be communicate to MB SW how many and which RCC or PLS bags are present.

For Back-Lab operation, MB RFID may for example able to receive data from BB SW also regarding BC pooling procedures for instance.

a. MB SW should receive a sort of list from BB SW where are included data as pooling barcode, BC barcode assembled, assembling date For example:

I201425236985;202500412536;202500412537; 202500412538;202500412539; 202500412540;30/11/2015

Where in bolt are written the BC barcode.

b. When pooling bag that will contain final PLT pool is positioned over the MB RFID, scanning barcode that identify that bag, data in the list should be written in the TAG previously applied.

Figure 4:
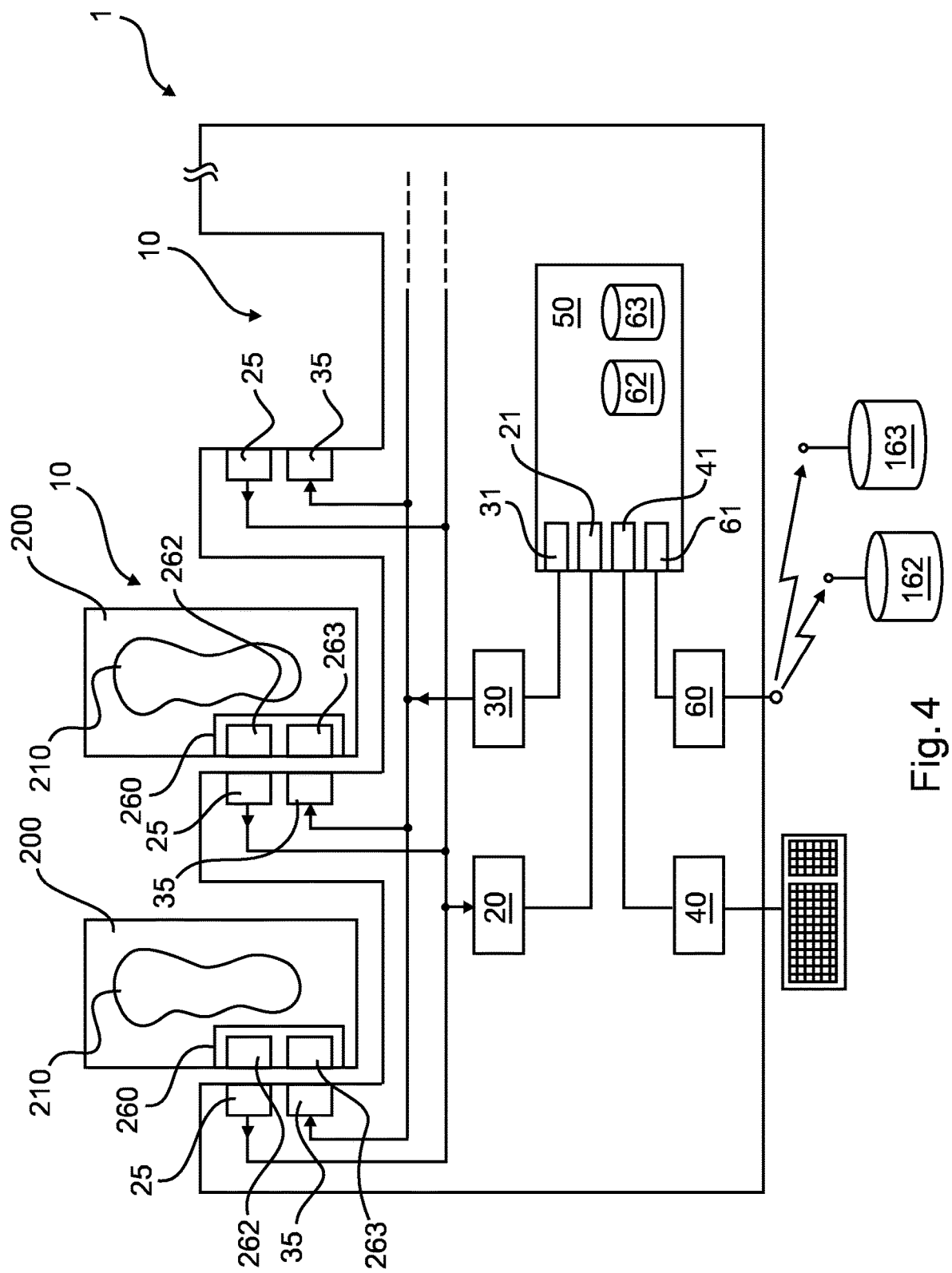
FIG. 4 illustrates a device for blood container processing according to an exemplary embodiment of the invention.

FIG. 4 illustrates a schematic buildup of a device according to an embodiment of the invention. The device for blood container processing 1 has one or more receptacles 10 for receiving one or more blood containers 200. A typical bold container 200 has a volume 210 for receiving blood. A typical blood container has a tag 260 for data storage. The tag 260 may have a read section 262 and/or a writing section 263. Both sections can be implemented in a single chip or may be implemented in separate chips. The reading section 262 may contain blood donator related information. This section may be realized as a read only section so that this information cannot be manipulated. The writing section 263 may contain information according to the interrelation between a donator and a recipient. The device 1 in FIG. 4 has a data storage reader unit 20, which may have a reading element 25. This reading element 25 may be arranged so that it can read the donator related information in data storage 262 on the container 200. The device may also have a data storage writing unit 30 with a data writing element 35. The writing element may be adapted for writing information, e.g. of information according to the interrelation between a blood donator and a blood recipient onto a respective storage 263 of the container 200. The device 1 may have a data processing unit 50 having data storage reader interface 21, a data storage writing interface 31, a user input interface 41 and a data base communicating interface 61. The data storage reader interface 21 is connected to the data storage reader 20 and the data storage writing interface 31 is connected to the data storage writer 30. The user input interface 41 may be connected to a user input device 40, which may be a keyboard or any other device for inputting recipient related information. The data base communicating interface 61 may be connected to a data communicating unit 60, which may be adapted for wireless or wire bounded data base connection to an external data base 162 or 163, or to internal data bases 62, 63. The data base storage unit 62 may be for interrelated blood recipient and donator information. The data base storage unit 63 may be for blood donator related information. Accordingly, the data base 162 may be for interrelated blood recipient and donator information, and the data base 163 may be for blood donator related information.

The invention claimed is:

1. A system for blood container processing comprising:
a plurality of blood containers (200), each blood container comprising a volume for receiving blood (210), and a data storage tag (260) comprising a reading data storage (262) and a writing data storage (263),
a plurality of receptacles (10) each configured to receive a plurality of blood containers (260) in parallel;
a data storage reader (20) for reading a data storage of the data storage tag (260) on the blood containers;
a data storage writer (30) for writing a data storage of the data storage tag on the blood containers;
wherein the data storage reader (20) and the data storage writer (30) are adapted to read and write the data storage tags of each of the plurality of blood containers in parallel;
wherein the data storage reader (20) has a plurality of data storage reading elements (25) wherein each of the plurality of receptacles is associated with one of the plurality of data storage reading elements, each data storage reading element being arranged so that it can read donator related information in the data storage of the data storage tags of the plurality of blood containers received in the associated receptacles and the data storage writer (30) has a plurality of data storage writing elements (35), wherein each of the plurality of receptacles is associated with one of the plurality of data storage writing elements, wherein the data storage reading element and the data storage writing element associated with the same receptacle are combined as a single reading writing unit so as to read and write a combined reading and writing data storage of a data storage tag on each of the plurality of blood containers;
a user interface (40) for inputting blood recipient related information;
a data processor (50) having a first discrete data base storage unit (62) having stored therein a data base for interrelated blood recipient and donator information, a second discrete data base storage unit (63) having stored therein a data base for blood donator related information, a data storage reader interface (21), a data storage writer interface (31), a user input interface (41) and a data base communicating interface (61);
a first discrete external data base (162) for interrelated blood recipient and donator information, and a second discrete external data base (163) for blood donator information with a wireless connection between each of the first and second discrete external databases and the data processor (50);
wherein the data storage reader (20) is communicatively connected to the data storage reader interface (21);
wherein the data storage writer (30) is communicatively connected to the data storage writer interface (31);
wherein the user interface (40) is communicatively connected to the user input interface (41);

wherein the data processor (50) is communicatively connected to a data base having stored therein blood donator related information, wherein the data storage reader (20) is adapted to read a blood donator identifier from a data storage of a plurality of blood containers;

wherein the data processor (50) is adapted to request for blood donator related information from one of the second discrete data base storage unit (63) and the second discrete external data base (163) based on the read blood donator identifier;

wherein the data processor (50) is adapted to request from one of the first discrete data base storage unit (62) and the first discrete external data base (162) for interrelated blood recipient and donator information based on the blood donator related information and the recipient related information input via the user interface (40), wherein the data processor (50) is adapted to control the data storage writer (30) to write blood donator related information into the data storage based on the interrelated blood recipient and donator information, and wherein the reading data storage (262) and the writing data storage (263) are realized as different chips, wherein the reading chip is adapted to be blocked from being written by the data storage writer which is used for writing the writing chip.

2. The system for blood container processing according to claim 1, wherein the interrelated blood recipient and donator information is information whether the donator blood matches the recipient.

3. The system for blood container processing according to claim 1, wherein the data storage tag (260) is an RFID tag.

4. The system for blood container processing according to claim 1, wherein blood donator related information comprises at least one of a group consisting of donator information, blood separation information, and blood component information.

5. The system for blood container processing according to claim 1, wherein the reading data storage (262) is capable of holding a blood donator identification.

6. The system for blood container processing according to claim 1, wherein the writing data storage (263) is capable of holding an interrelated blood donator and recipient identification.

* * * * *